United States Patent
Sramek et al.

(10) Patent No.: US 12,162,993 B2
(45) Date of Patent: Dec. 10, 2024

(54) METHOD OF OBTAINING TEREPHTHALIC ACID FROM WASTE POLYETHYLENE TEREPHTHALATE

(71) Applicant: JBPV s.r.o., Protivanov (CZ)

(72) Inventors: Jaromir Sramek, Satalice (CZ); Michal Trzewiczek, Miedzylesie (PL); Karel Travnicek, Ochoz (CZ)

(73) Assignee: JBPV s.r.o., Protivanov (CZ)

( * ) Notice: Subject to any disclaimer, the term of this patent is extended or adjusted under 35 U.S.C. 154(b) by 1066 days.

(21) Appl. No.: 16/979,748

(22) PCT Filed: Mar. 11, 2019

(86) PCT No.: PCT/CZ2019/000014
§ 371 (c)(1),
(2) Date: Sep. 10, 2020

(87) PCT Pub. No.: WO2019/174656
PCT Pub. Date: Sep. 19, 2019

(65) Prior Publication Data
US 2021/0017353 A1    Jan. 21, 2021

(51) Int. Cl.
| | | |
|---|---|---|
| *C08J 11/16* | (2006.01) | |
| *B01D 11/04* | (2006.01) | |
| *B01J 19/00* | (2006.01) | |
| *B01J 19/12* | (2006.01) | |
| *B01J 20/20* | (2006.01) | |
| *C07C 51/48* | (2006.01) | |
| *C07C 63/26* | (2006.01) | |
| *C08J 11/08* | (2006.01) | |
| *C08J 11/12* | (2006.01) | |

(52) U.S. Cl.
CPC ........... *C08J 11/16* (2013.01); *B01D 11/0492* (2013.01); *B01J 19/0066* (2013.01); *B01J 19/126* (2013.01); *B01J 20/20* (2013.01); *C07C 51/48* (2013.01); *C07C 63/26* (2013.01); *C08J 11/08* (2013.01); *C08J 11/12* (2013.01); *C08J 2367/03* (2013.01)

(58) Field of Classification Search
CPC ...................................................... C08J 11/16
See application file for complete search history.

(56) References Cited

U.S. PATENT DOCUMENTS

| | | | |
|---|---|---|---|
| 3,222,299 A | 12/1965 | MacDowell | |
| 3,501,420 A | 3/1970 | Stevenson | |
| 4,078,143 A | 3/1978 | Malik et al. | |
| 4,605,762 A | 8/1986 | Mandoki | |
| 5,254,666 A * | 10/1993 | Benzaria | ............... C07C 51/412 |
| | | | 562/480 |
| 5,412,126 A * | 5/1995 | King | ....................... C07C 51/02 |
| | | | 554/185 |
| 7,897,651 B2 | 3/2011 | Ikenaga | |
| 9,757,664 B2 * | 9/2017 | McGhee | ................. C11B 9/025 |
| 2005/0096482 A1* | 5/2005 | Tamada | .................... C08J 11/24 |
| | | | 560/89 |
| 2006/0074136 A1 | 4/2006 | Smith et al. | |
| 2010/0133088 A1* | 6/2010 | Hajek | ..................... C08J 11/22 |
| | | | 204/157.87 |

FOREIGN PATENT DOCUMENTS

| | | |
|---|---|---|
| CN | 1594268 | 3/2005 |
| CZ | 288622 | 8/2001 |
| CZ | 299176 | 5/2008 |
| CZ | 299244 | 5/2008 |
| GB | 2123403 | 2/1984 |
| JP | 2002060369 | 2/2002 |
| JP | 2015036393 | 2/2015 |
| WO | WO 1997/024310 | 7/1997 |
| WO | WO 2006/039872 | 4/2006 |
| WO | WO 2009/010435 | 1/2009 |
| WO | WO 2015/190941 | 12/2015 |

OTHER PUBLICATIONS

International Search Report and Written Opinion of Application No. PCT/CZ2019/000014, date of mailing May 29, 2019.

* cited by examiner

*Primary Examiner* — Irina Krylova
(74) *Attorney, Agent, or Firm* — Mark S. Cohen; PEARL COHEN ZEDEK LATZER BARATZ LLP

(57) ABSTRACT

Method of obtaining terephthalic acid from waste polyethylene terephthalate by depolymerization with microwave heating of the reaction mixture, and its subsequent purification, wherein, after depolymerization, the mixture of products of the depolymerization reaction is mixed with water, a solid phase is separated from the formed mixture, the obtained solution is extracted with water-immiscible organic solvent and, after separation of phases, dissolved impurities are removed from the aqueous phase by its contact with a sorbent that is then separated, wherein, after separation of the sorbent, terephthalic acid is precipitated from the solution by its acidification and subsequently separated from the formed suspension.

3 Claims, No Drawings

METHOD OF OBTAINING TEREPHTHALIC ACID FROM WASTE POLYETHYLENE TEREPHTHALATE

CROSS-REFERENCE TO RELATED APPLICATIONS

This application is a National Phase Application of PCT International Application No. PCT/CZ2019/000014, International Filing Date Mar. 11, 2019, claiming priority to Czech Application No. PV 2018-120, filed Mar. 12, 2018, which are hereby incorporated by reference in their entirety.

FIELD OF THE INVENTION

The present invention falls within the field of processing waste polymers and relates to a method of obtaining terephthalic acid from waste polyethylene terephthalate, and its subsequent purification.

BACKGROUND ART

For their good chemical stability, polyesters, such as, for instance, polyethylene terephthalate, abbrev. PET, are frequently utilized in producing fibres, various coatings, or beverage bottles. In recent decades, recycling, particularly of the last above mentioned products, has gained great importance because of enormous increase of their production. Recently, special position among recycling methods is being gained by chemical processing of PET bottles to monomers wherein, in the case of heavily contaminated PET material, chemical depolymerization based on solvolysis is advantageous.

Document CZ299244 discloses a method of high-temperature hydrolysis of waste polyethylene terephthalate to basic salt of terephthalic acid and ethylene glycol in a reaction system consisting of extruder and tubular reactor in a two-stage process. In the first stage, the waste PET is degraded by simultaneously running extrusion hydrolysis and glycolysis at the pressure from 3.5 to 9.0 MPa and the temperature from 240 to 295° C., and in the second stage, the melt of oligomeric products of the reactive extrusion from the first stage is continuously basically hydrolyzed at elevated pressure by continuous adding of aqueous solution of alkaline hydroxide or ammonia. A characteristic feature of the above mentioned process is degradation of polyethylene terephthalate at temperature higher than temperature of its crystallization. The hydrolysis results in the solution of ammonium or sodium salt of terephthalic acid and ethylene glycol in water, wherein conversion of PET is not lower than 97%. Method of preparing oligomers of terephthalic acid and ethylene glycol by transesterification of waste PET is disclosed in documents U.S. Pat. Nos. 3,222,299 and 4,078,143. The process comprises glycolysis of waste PET at temperature ranging between 90° C. and 250° C. for obtaining PET oligomers which are subsequently used as raw material in synthesis of unsaturated polyester resins or polyurethanes. Another document U.S. Pat. No. 4,605,762 discloses a method of hydrolysis of waste PET in an autoclave at temperature 200 to 300° C. and minimum pressure of 1.5 MPa using overheated steam. In the process disclosed in document WO97/24310, hydrolysis of waste PET is carried out using aqueous solution of salt of alkaline hydroxide to obtain aqueous solution of salt of terephthalic acid and ethylene glycol. Terephthalic acid is obtained by neutralization of the hydrolyzate with strongly acidic solution and purified by crystallization from a solvent. Degradation of polyethylene terephthalate by transesterification with methanol is disclosed in document U.S. Pat. No. 3,501,420 where methanolysis is carried out at the temperature from 160 to 240° C. in pressure reactors at the pressure up to 7.0 MPa under a marked excess of methanol. The advantage of this method of degrading polyethylene terephthalate is possibility of using PET waste containing also coloured polymer. Document CZ288622 discloses a method of chemical recycling of non-sorted crushed waste PET to terephthalic acid and ethane diol by continuous two-stage hydrolysis where, in the first stage, steam is injected into the polymer melt and, in the second stage, products of the first stage of hydrolysis react with ammonium hydroxide. Then, terephthalic acid is precipitated from its aqueous solution with inorganic acid separated by filtration, and ethane diol is separated by rectification from the solution of hydrolysis products. The method of chemical recycling of waste PET to terephthalic acid and ethane diol by two-stage hydrolysis is also disclosed in document CZ299176. In the first stage, waste polyethylene terephthalate undergoes glycolysis at the temperature from 220 to 380° C. and the pressure of 18.0 MPa with presence of water, wherein ethylene glycol is added in the amount of up to 15% by weight relative to polymer waste. In the second stage, the mixture of PET oligomers undergoes ammonolysis in aqueous medium to obtain ammonium terephthalate. After it terephthalic acid is separated from the aqueous solution by addition of an inorganic acid and subsequently filtered off from the mixture. Document JP 2002060369 discloses recycling of plastic waste consisting mainly of polyethylene terephthalate by transesterification with methanol under elevated pressure to obtain dimethyl terephthalate. In the following stage, dimethyl terephthalate is purified by vacuum distillation and then it undergoes hydrolysis with steam to produce terephthalic acid and aqueous solution of methanol. The obtained terephthalic acid is of high purity and, it can fully replace the petrochemically obtained acid in synthesis of polymers or terephthalates. In the well known depolymerization of PET carried out by transesterification at temperature of boiling alcohol used in synthesis under atmospheric pressure, the mixture of PET oligomers is, after depolymerization, hydrolyzed to terephthalic acid or its salts. Isolation of the salt of terephthalic acid from the post-reaction mixture comprises its cooling to temperature below the boiling point of water under normal pressure, dilution of the reaction medium with water to dissolve the salt of terephthalic acid, addition of water to the reaction mixture to induce phase separation of the aqueous solution of the dissolved salt of terephthalic acid from the organic phase of alcohol used in depolymerization, phase separation of the aqueous phase from the organic phase, precipitation of terephthalic acid from the aqueous phase by adding inorganic acid, separation of crystals of terephthalic acid by filtration and purification by washing with solvents and water, and regeneration of alcohol used in depolymerization of PET waste in the first technological stage. The terephthalic acid produced in this way is characterized by high purity, comparable with the acid produced by petrochemical procedures, and the above mentioned method is, in comparison with other known technologies, characterized by lower consumption of energy and, thus, lower costs for processing PET waste. Continuous method of producing pure terephthalic acid and ethylene glycol is disclosed in document GB2123403, wherein the process is carried out in the presence of active carbon in aqueous solution during hydrolysis of waste PET under high pressure and at the temperature from 200° C. to 300° C. The post-reaction mixture is then filtered and cooled; the cooling of the solution results in crystallization of terephthalic acid. The crystals of terephthalic acid are separated from the mother liquor by filtration or centrifugation and ethylene glycol is obtained from the mother liquor by distillation. Document WO2015190941 discloses a method of recycling polyethylene terephthalate based on multiple transesterification of the polymeric material using various alcohols. In the first stage, PET particles are treated with monovalent high-boiling or multivalent alcohol or their mixtures at the temperature from 190 to 265° C., preferably with addition of phenol. Produced ethylene glycol is removed from the reaction media by distillation under normal or reduced pressure. In the second step, the resulting mixture of PET oligomers is mixed with low-boiling alcohol or low-boiling alcohol mixture, and again undergoes transesterification at elevated temperature with presence of a catalyst under continuous stirring of the batch of transesterification reactor. In the third step, water is added to the reaction solution and simple esters of terephthalic acid are hydrolyzed with mineral acid. Suspension of crystals of terephthalic acid is filtered, the acid is isolated in this way is washed with water and dried. Document WO2006/039872 discloses a two-stage method of recycling waste polyethylene terephthalate, where in the first step, PET flakes are hydrolyzed with water at the temperature from 220 to 280° C. under elevated pressure with the weight ratio of water to PET in the range of 1:1 to 1:8. The reaction mixture from the first stage, containing oligomers of terephthalic acid and PET, is cooled to the temperature below 60° C. and, after crystallization, terephthalic acid is separated by filtration. After the first stage of hydrolysis, the crystals of oligomers contaminated with PET are re-hydrolyzed with water. In this second stage of hydrolysis, conditions used are the same as in the first stage. Raw terephthalic acid from the second stage of hydrolysis is dissolved in ammonia liquor and then purified using solid sorbents, particularly active carbon. The solution of ammonium salt of terephthalic acid deprived of organic contaminants is acidified with sulphuric acid to obtain a suspension of crystals of terephthalic acid in water.

It follows from literature that the key step is decomposition of waste PET by depolymerization to oligomers having a low molecular weight in combination with hydrolysis in water or in alkaline aqueous solutions. Depolymerization of PET is an energy demanding process requiring radical thermal conditions. The way of providing energy and its utilization in the process determines profitability of chemical processing of the waste polymer. New trend in processing waste PET is using of microwave radiation as a source of energy. Document WO2009/010435 discloses a method of chemical depolymerization of waste polyethylene terephthalate by action of microwave radiation using solvolysis in the presence of catalyst where, in the first stage, waste polyethylene terephthalate is mixed with an activator strongly absorbing microwaves and the mixture is placed into microwave field. By action of microwave radiation having frequency from 915 to 2450 MHz and a power output of the radiation source 0.1 to 0.5 kW per 1 kg of batch at the temperature from 230 to 330° C. and atmospheric pressure, the waste PET is melted; in the second stage, it is exposed to continuing microwave radiation and undergoes solvolysis, i.e. acidic or alkaline hydrolysis, alcoholysis or glycolysis in presence of a catalyst at atmospheric pressure to produce terephthalic acid, its salts or esters, and ethylene glycol. Activators in the first stage of the process are usually either polar liquids from the group of monovalent alcohols, diols, ketones, organic acids, such as terephthalic acid, p-toluenesulphonic acid, formic acid, acetic acid, or water, possibly mixtures thereof, or silicon carbide, tungsten carbide, ferrite, magnetite or activated charcoal, wherein the amount of activator is up to 30% by weight relative to weight of PET. In the second stage of the process of acidic hydrolysis of oligomers, either heterogeneous acidic catalysts, such as montmorillonite, zeolite, ion-exchange resins, zeolites, phosphoric acid deposited on a carrier, copper(II), ferric, aluminium, antimony(III), or bismuth(III) chlorides or acetates, or homogeneous catalysts, such as p-toluenesulphonic acid, formic acid, acetic acid, benzoic acid, terephthalic acid or sulphuric acid, are used. In the case the second stage is carried out by alkaline hydrolysis, strong bases, such as hydroxides of alkaline metals, are used, possibly in the presence of catalysts of phase transfer.

The aim of the present invention is to provide a new method of preparing terephthalic acid from waste polyethylene terephthalate, that will enable production of terephthalic acid of high purity with maintained low costs of equipment and its operation.

SUMMARY OF INVENTION

The set aim is achieved by the invention that relates to a method of obtaining terephthalic acid from waste polyethylene terephthalate by depolymerization with microwave heating of the reaction mixture, and its subsequent purification. The subject matter of the invention is that, after depolymerization, the mixture of products of the depolymerization reaction is stirred with water, solid phase is separated from the produced mixture, the obtained solution is extracted with a water-immiscible organic solvent and, after separation of phases, dissolved impurities are removed from the aqueous phase by its contact with a sorbent that is subsequently separated, wherein, after separation of the sorbent, terephthalic acid is precipitated from the solution by its acidification and subsequently separated from the formed suspension.

In preferable embodiment, the extraction is carried out in an extraction apparatus, wherein the extraction agent circulates in a closed circle and, after separation of phases, maximum of 30% of the amount of the phase of extraction agent is separated, from which the extraction agent is regenerated and subsequently recycled back into the extraction, the remaining amount of the phase of extraction agent being recycled directly into the extraction.

In another preferable embodiment, the extraction is carried out with the extraction agent selected from the group of: monovalent alcohols having number of carbon atoms in the range of 4 and 10, preferably 8, or aliphatic hydrocarbons having number of carbon atoms in the range of 6 and 12, or benzene, or liquid aromatic hydrocarbons substituted with one or more alkyl groups, or chlorinated hydrocarbons saturated, unsaturated or aromatic, or mixtures thereof in any ratio.

Further, it is preferable when active carbon or bleaching clay, and/or mixture thereof are used as a sorbent.

In another preferable embodiment, the process of depolymerization is carried out continuously in two serial-interconnected reactors adapted for exhaust of gaseous phase, of which the second reactor is adapted for operation under reduced pressure.

It is further preferable when the reaction mixture in the reactors is, during the depolymerization process, transported and at the same time stirred using a screw agitator installed in both reactors that is adapted for controlling the holding time of the reaction mixture in the reactor.

The present invention provides for new and higher effect in that it enables using of waste polyethylene terephthalate of various purity, including coloured PET bottles, shows low costs, both investment and operational, and, finally, according to this method of the invention provides terephthalic acid of purity comparable with the acid obtained by petrochemical procedures.

The below disclosed examples of particular embodiment in any case do not limit the scope of protection defined in claims, but only explain the subject of the invention.

EXAMPLES

The two-stage reaction system used in the process of depolymerization of waste polyethylene terephthalate by alkaline hydrolysis consists of two serial-interconnected reactors adapted for continuous operation that are provided with a source of microwave radiation, jacketed-vessel steam heater, and a screw transporter adapted both for stirring the reaction mixture during its transport from the reactor inlet to the reactor outlet and for controlling holding time of the reaction mixture in the reaction zone. The two-stage reaction system operates continuously with constant feed of raw material and withdrawal of reaction products at the outlet from the reaction system. The mixture of crushed waste polyethylene terephthalate, granulated alkaline hydroxide and water is continuously fed to the hopper of the first-stage reactor, wherein feed in the case of NaOH relative to waste PET is in the range of 40 and 42 kg per 100 kg of crushed PET and in the case of KOH is in the range of 56 and 59 kg per 100 kg of crushed PET. The mixture is agitated in the hopper and transported into the intake part of the reactor where it is further stirred with a screw agitator and exposed to action of microwaves from the source of microwave radiation. By action of microwave radiation, the reaction mixture is heated above 150° C., which starts the depolymerization reaction alkaline hydrolysis. The mixture is stirred by the screw agitator and transported through the reactor to its outlet part, wherein the continuous depolymerization reaction takes place. Vapours of ethylene glycol released during the reaction are drawn off, together with steam, to a condenser.

The reaction mixture containing products of alkaline hydrolysis is subsequently transported by gravity flow via a separating closure into the second-stage reactor operating under reduced pressure is in the range of 10 and 20 kPa abs., from which ethylene glycol formed during the depolymerization is removed through exhaust.

In the first purification stage, the bulk mixture of products from the second-stage reactor is mixed with water, in which alkaline salt of terephthalic acid and its oligomers produced during the reaction is dissolved and a solid phase of impurities, non-reacted components, and other solid admixtures is subsequently separated.

The obtained solution proceeds to further purification stage of the process where it is continuously extracted with a solvent immiscible with water selected from the group of: monovalent alcohols having number of carbon atoms in the range of 4 and 10, preferably 8, aliphatic hydrocarbons having number of carbon atoms in the range of 6 and 12, liquid aromatic hydrocarbons substituted with one or more alkyl groups, chlorinated hydrocarbons saturated, unsaturated or aromatic. The extraction is carried out at the temperature in the range of 20 and 80° C., preferably 50° C., under atmospheric pressure, wherein maximum weight of the extraction agent is 50% at most of weight of the solution being extracted. After the extraction and separation of phases, maximum of 30% of the amount of the extraction agent phase is separated from it; the extraction agent is regenerated from this part and subsequently recycled into the extraction. The remaining part of the extraction agent phase is recycled directly back into the extraction process.

A sorbent, preferably powdered active carbon, is added to the aqueous phase after extraction at the temperature in the range of 20 and 80° C., preferably 50° C., the sorbent being subsequently separated.

Adsorption of impurities by addition of powdered active carbon is not the only solution. Another alternative is continuous flow of the solution through a layer of granulated sorbent, where the residual sorbent is subsequently removed from the solution by filtration.

After the sorbent is filtered off, terephthalic acid is precipitated from the solution at the temperature in the range of 20 and 80° C., preferably 50° C., by acidifying the solution so that pH in the resulting suspension would be lower than 3.5. The precipitate of terephthalic acid is subsequently separated by filtration, washed with demineralized water, and dried under vacuum.

Example 1

The mixture of 20 kg/h of waste polyethylene terephthalate, 8.4 kg/h of sodium hydroxide, and 4 kg/h of water is continuously fed to the hopper of the first-stage reactor under atmospheric pressure. The reaction mixture in the first-stage reactor is microwave-heated to the temperature of 110° C. and then it is transported, at gradually increasing temperature, through the reactor towards its outlet, wherein the rate of transport of the reaction mixture is controlled, so that the holding time of the mixture in the reactor would be at least 15 minutes at the temperature above 150° C. After the reaction mixture has passed via the separating closure to the second-stage reactor, the temperature is maintained in the range of 150 to 165° C. at the pressure of 15 kPa abs. using microwave radiation and steam heating in this jacket.

The bulk mixture leaving the second-stage reactor is dissolved in water to provide solution of disodium salt of terephthalate having concentration 12.5% by weight at flow rate 192 kg/h with dispersed non-dissolved impurities that are subsequently filtered off on a screen. The solution of disodium salt of terephthalic acid is then continuously extracted on an extraction column with iso-octanol at the temperature of 45° C. to separate water-soluble organic impurities, wherein iso-octanol of 80 kg/h is pumped from a reservoir into the lower part of the extraction column and 192 kg/h of the solution of disodium salt of terephthalic acid is pumped onto the column head. The extraction agent is circulated in a closed circle, wherein 20 kg/h of the extraction agent phase coming out of the extraction column is directed to the vacuum evaporator to separate the extraction agent from extracted substances, wherein the evaporated extraction agent is, after condensation, recycled into the reservoir.

After the extraction, the solution of disodium salt of terephthalic acid is transferred into a vessel fitted with a mechanical stirrer, where active carbon is added in the amount corresponding to 1% by weight and the resulting suspension is stirred at the temperature of 52° C. for 2 hours. Subsequently, the mixture is filtered at the temperature of 50° C.±5° C. through a candle filter, where 189.5 kg/h of clear solution of disodium salt of terephthalic acid is obtained in colour 90 to 100 APHA. The resulting solution flows into a precipitation vessel of the type of a mixer where nitric acid is added at the temperature of 45° C. in such quantity that, after mixing, pH value would be 3.3, which results in precipitation of terephthalic acid. After this it is separated from the mother liquors on a filtration centrifuge, where it is subsequently washed with water at the temperature of 61° C., which results in removal of sodium nitrate and excess of nitric acid. Terephthalic acid is then transferred into a drying oven where it is dried at 70° C. under reduced pressure. Thus obtained terephthalic acid shows purity comparable with terephthalic acid produced from petrochemical raw materials.

Example 2

The procedure according to example 1 with the difference that n-hexane is used for extraction, active carbon is added as a sorbent to the aqueous phase after extraction, and sulphuric acid is used in final precipitation of terephthalic acid from the solution.

Example 3

The procedure according to example 1 with the difference that toluene is used for extraction, bleaching clay is added as a sorbent to the aqueous phase after extraction, and hydrochloric acid is used in final precipitation of terephthalic acid from the solution.

Example 4

The procedure according to example 1 with the difference that perchloroethylene is used for extraction, a mixture of active carbon and bleaching clay is added as a sorbent to the aqueous phase after extraction, and acetic acid is used in final precipitation of terephthalic acid from the solution.

The invention claimed is:
1. A method of obtaining and purifying terephthalic acid from waste polyethylene terephthalate, the method comprising:
depolymerizing with microwave heating and alkaline hydrolysis a reaction mixture comprising the waste polyethylene terephthalate, wherein the depolymerizing is carried out continuously in two steps in two serial-interconnected reactors adapted for exhaust of a gaseous phase, and wherein the serial-interconnected reactors consist of a first reactor and a second reactor, and wherein the reaction mixture is transported by gravity flow via a separating closure from the first reactor to the second reactor, and wherein the first reactor is operated at atmospheric pressure, the second reactor is operated under reduced pressure of 10 to 20 kPa to remove mono-ethylene glycol, and wherein the depolymerizing produces a reaction mixture of products of the alkaline hydrolysis;
mixing the reaction mixture of the products of the alkaline hydrolysis with water to obtain an aqueous phase and a solid phase;
separating the solid phase from the aqueous phase to obtain a solution;
extracting the solution with an extraction agent that is a water-immiscible organic solvent selected from the group consisting of iso-octanol, n-hexane, toluene, and perchloroethylene to form two mutually immiscible liquid phases, wherein the extracting is carried out in an extraction apparatus, wherein the extraction agent circulates in a closed circle, and wherein a maximum of 30% of an amount of the extraction agent phase is separated from extracted substances, from which the extraction agent is regenerated and subsequently recycled back into the extraction apparatus, and wherein a remaining amount of the extraction agent phase is recycled directly into the extraction apparatus, the two mutually immiscible liquid phases resulting from the extracting are an aqueous solution and an organic solvent phase;
separating the aqueous solution and the organic solvent phase;
removing dissolved impurities from the aqueous solution by contacting the aqueous solution with a sorbent;
filtering the aqueous solution;
acidifying the filtered aqueous solution to produce a suspension and a precipitate of terephthalic acid; and
separating the precipitate of the terephthalic acid from the suspension by filtration.
2. The method of claim 1, wherein active carbon, bleaching clay, or a mixture thereof is the sorbent.
3. The method of claim 1, wherein during the depolymerizing, the reaction mixture in the two reactors is transported and concurrently stirred with a screw agitator installed in both reactors adapted for controlling holding time of the reaction mixture in the reactors.

* * * * *